(12) United States Patent
Kyushima et al.

(10) Patent No.: US 6,650,049 B1
(45) Date of Patent: Nov. 18, 2003

(54) PHOTOMULTIPLIER TUBE (75) Inventors: Hiroyuki Kyushima, Hamamatsu (JP); Akira Atsumi, Hamamatsu (JP); Hideki Shimoi, Hamamatsu (JP); Tomoyuki Okada, Hamamatsu (JP); Masuo Ito, Hamamatsu (JP)

(73) Assignee: Hamamatsu Photonics K.K., Hamamatsu (JP)

( * ) Notice: Subject to any disclaimer, the term of this patent is extended or adjusted under 35 U.S.C. 154(b) by 0 days.

(21) Appl. No.: 09/701,278

(22) PCT Filed: Jun. 1, 1999

(86) PCT No.: PCT/JP99/02923

§ 371 (c)(1), (2), (4) Date: Nov. 28, 1999

(87) PCT Pub. No.: WO99/63575

PCT Pub. Date: Dec. 9, 1999

(30) Foreign Application Priority Data

Jun. 1, 1998 (JP) .............................. 10-151596
Jun. 1, 1998 (JP) .............................. 10-151603

(51) Int. Cl.[7] ................................ H01J 43/04
(52) U.S. Cl. ................ 313/532; 313/536; 313/533
(58) Field of Search ...................... 313/532, 525, 313/538, 536, 533, 103 R; 250/366

(56) References Cited

U.S. PATENT DOCUMENTS 5,035,179 A    7/1991  Bender et al.
5,504,386 A  * 4/1996  Kyushima et al. ...... 313/103 R
5,619,100 A  * 4/1997  Kyushima et al. .......... 313/533
5,744,908 A  * 4/1998  Kyushima ................... 313/533

FOREIGN PATENT DOCUMENTS

| CN | 1041900 A | | 5/1990 |
|---|---|---|---|
| EP | 0 622 827 | * | 2/1994 |
| EP | 0 565 247 B1 | | 5/1997 |
| JP | 6-295704 A | | 10/1994 |
| JP | 9-320511 | | 12/1997 |
| JP | 10-214589 | | 8/1998 |
| JP | 10-241623 | | 9/1998 |

* cited by examiner

Primary Examiner—Edward J. Glick
Assistant Examiner—Elizabeth Gemmell
(74) Attorney, Agent, or Firm—Oliff & Berridge PLC (57) ABSTRACT

To reduce the size of a photomultiplier tube (1), a side tube (2) is fixedly secured by welding to a stem plate (4) while an inner surface (2c) of the lower portion (2a) of the side tube (2) is maintained to be in contact with an outer edge (4b) of the stem plate (4). As a result, there is no projection like a flange at the lower portion of the photomultiplier tube (1). Therefore, though it is difficult to perform resistance welding, the outside dimensions of the photomultiplier tube (1) can be decreased, and the side tubes (9) can densely abut to one another even if the photomultiplier tubes (2) are arranged when applied. Hence, high-density arrangement of photomultiplier tubes (1) are realized by assembling metallic stem plate (4) and the side tube (2) by, for example, laser welding.

8 Claims, 11 Drawing Sheets

PHOTOMULTIPLIER TUBE

TECHNICAL FIELD

The present invention relates to a photomultiplier tube designed to detect through multiplication weak light radiated onto a faceplate.

BACKGROUND ART

Photomultiplier tubes are produced at various sizes to suit different uses. Conventional photomultiplier tubes are generally configured of a hermetically sealed vessel constructed entirely of glass. This type of photomultiplier tube has a substantially cylindrical glass side tube with a planar and substantially circular stem fitted on the bottom open end. A gas burner is applied to the area in which the periphery of the stem contacts the inner surface of the side tube, and the two are fused together by heat to form an airtight seal. A planar and substantially circular transparent faceplate is fused in the same manner to the top opening of the side tube, forming an airtight seal. A glass exhaust tube is provided in the stem, forming a fluid connection with the inside of the hermetically sealed vessel. After evacuating the vessel through the exhaust tube, an alkaline metal vapor is introduced into the vessel to form a photocathode on the inner surface of the faceplate and also to activate the secondary electron emitting surface of the electron multiplying section disposed inside the vessel.

As described above, the side tube and stem are fused together with heat from a gas burner in order to construct a photomultiplier tube having an airtight glass vessel. Further, after introducing the alkaline metal vapor, the exhaust tube is pinched off and sealed with the gas burner. Accordingly, it is necessary to prevent heat from damaging the electron multiplying section. Therefore, it has been necessary to maintain a distance of about 20–30 mm from the airtight fused junctions to the bottom of the electron multiplying section. Unfortunately, this inhibits downsizing of the photomultiplier tube.

While it depends on the application, the advantages of downsizing a photomultiplier tube are generally great. One example is a sanitation monitor that is used for detecting bacteria in restaurants and the like. The sanitation monitor employs a photomultiplier tube to detect light that is emitted from reactions between drugs and bacteria. Since this type of monitoring device should be portable and easy to use, the photomultiplier tubes used in the monitor must be small. A small enough photomultiplier tube can be mounted directly on a circuit board and treated in the same way as a resistor or capacitor, thereby making the tubes more convenient for device construction.

In light of these demands, small photomultiplier tubes having metal side tubes have been developed for practical uses in recent years. An example of this type of photomultiplier tube described in Japanese Unexamined Patent Application Publication Nos. HEI-5-290793 and HEI-9-306416 has a metal side tube having a polygonal cross-section with a flange portion protruding laterally from the bottom of the tube. Similarly, the metal stem plate is provided with a flange portion that protrudes laterally. The flange portions of the side tube and stem plate overlap and are fused through resistance welding to form a hermetically sealed vessel. Resistance welding is performed in such a way that current is applied to the joining parts, which are heated through the heat generated from resistance. When the parts reach an appropriate temperature, pressure is applied to weld them together. Hence, it is possible to avoid the thermal affects that resistance welding has on the electron multiplying section. As a result, the distance between the stem plate and electron multiplying section can be reduced, thereby achieving a smaller photomultiplier tube that is shorter in the axial direction.

With a photomultiplier tube of this construction, however, the flange portions required for resistance welding interfere with the use of the tube. For example, when photomultiplier tubes are used in gamma cameras and the like, in particular, it is necessary to arrange a plurality of photomultiplier tubes closely together and form a large area for receiving light. With this configuration, the flange portions contact other flange portions, forming dead spaces. Dead spaces are a hindrance to achieving a high-performance detecting device.

DISCLOSURE OF THE INVENTION

The present invention has been made to solve the above-described problems, and accordingly it is an object of the present invention to provide a photomultiplier tube and a method for manufacturing a smaller multiplier tube.

The above object will be attained by a photomultiplier tube having a faceplate, a photocathode for emitting electrons in response to light incident on the faceplate, an electron multiplying section, disposed inside an airtight vessel, for multiplying the electrons emitted from the photocathode, and an anode for outputting an output signal based on the electrons multiplied by the electron multiplying section, characterized in that the airtight vessel is formed by:

a stem plate for fixedly supporting the electron multiplying section and the anode with stem pins;

a side tube with the stem plate fixed on one open end, the side tube being formed of metal and enclosing the electron multiplying section and the anode; and the faceplate fixed on the other open end of the side tube, and that an inner surface of a lower portion of the side tube is in contact with an outer edge of the stem plate, at least a portion of the stem plate contacting the inner surface of the lower portion of the side tube is formed of metal, the portion thereof including the outer edge of the stem plate, and the side tube is welded to the stem plate.

In the photomultiplier tube as defined above, the side tube is fixedly secured by welding to the stem plate while the inner surface of the lower portion of the side tube is maintained to be in contact with the outer edge of the stem plate, with the result that there is no projection like a flange at the lower portion of the photomultiplier tube. Therefore, though it is difficult to perform resistance welding, the outside dimensions of the photomultiplier tube can be decreased, and the side tubes can densely abut to one another even if the photomultiplier tubes are arranged when applied. Hence, high-density arrangement of photomultiplier tubes are realized by assembling metallic stem plate and the side tube by, for example, laser welding.

It is preferable that the side tube have a free end at the lower portion thereof, allowing the stem plate to slide along the inner surface of the side tube. With this configuration, the stem plate can be inserted through the open end of the side tube, such that the edge surface of the stem plate contacts and slides inwardly on the inner surface of the lower portion of the side tube for adjusting and determining the position of the stem plate. As a result, the distance between the electron multiplying section, which is fixed to the stem plate, and the photocathode can easily be adjusted before the welding process.

It is further preferable that the metal side tube is fusion welded to the stem plate. In contrast to resistance welding, a fusion welding method does not require that pressure be added to the portions of the side tube and stem plate that are being joined. Accordingly, residual stress that can lead to cracking during operations is not generated at this junction, thereby greatly improving durability of the apparatus.

It is preferable that the fusion welding be laser welding or electron beam welding. The methods of laser welding and electron beam welding generate little heat at the junction. Therefore, the glass tablets fixing the stem pins to the stem plate are not apt to crack from the effects of the heat when the stem pins are near the side tube. Accordingly, it is possible to move these stem pins closer to the side tube and expand the electron multiplying section laterally, creating a greater electron receiving surface area in the electron multiplying section.

Entirety of the stem plate can be formed of metal. Otherwise, the stem plate may include a metal stem support member, and a glass stem plate wherein the metal stem support member is in contact with the inner surface of the lower portion of the side tube.

A tapered surface can be formed in the inner surface of the lower portion of the side tube and a tapered edged surface can be formed in the stem plate to conform to the tapered surface of the side tube, so that the tapered surface of the side tube and the tapered edged surface of the stem plate are in contact with each other.

In addition, a bottom surface of the stem plate and a bottom surface of the side tube may be flush with each other.

BEST MODE FOR CARRYING OUT THE INVENTION

A photomultiplier tube according to preferred embodiments of the present invention will be described while referring to the accompanying drawings.

Figure 1:
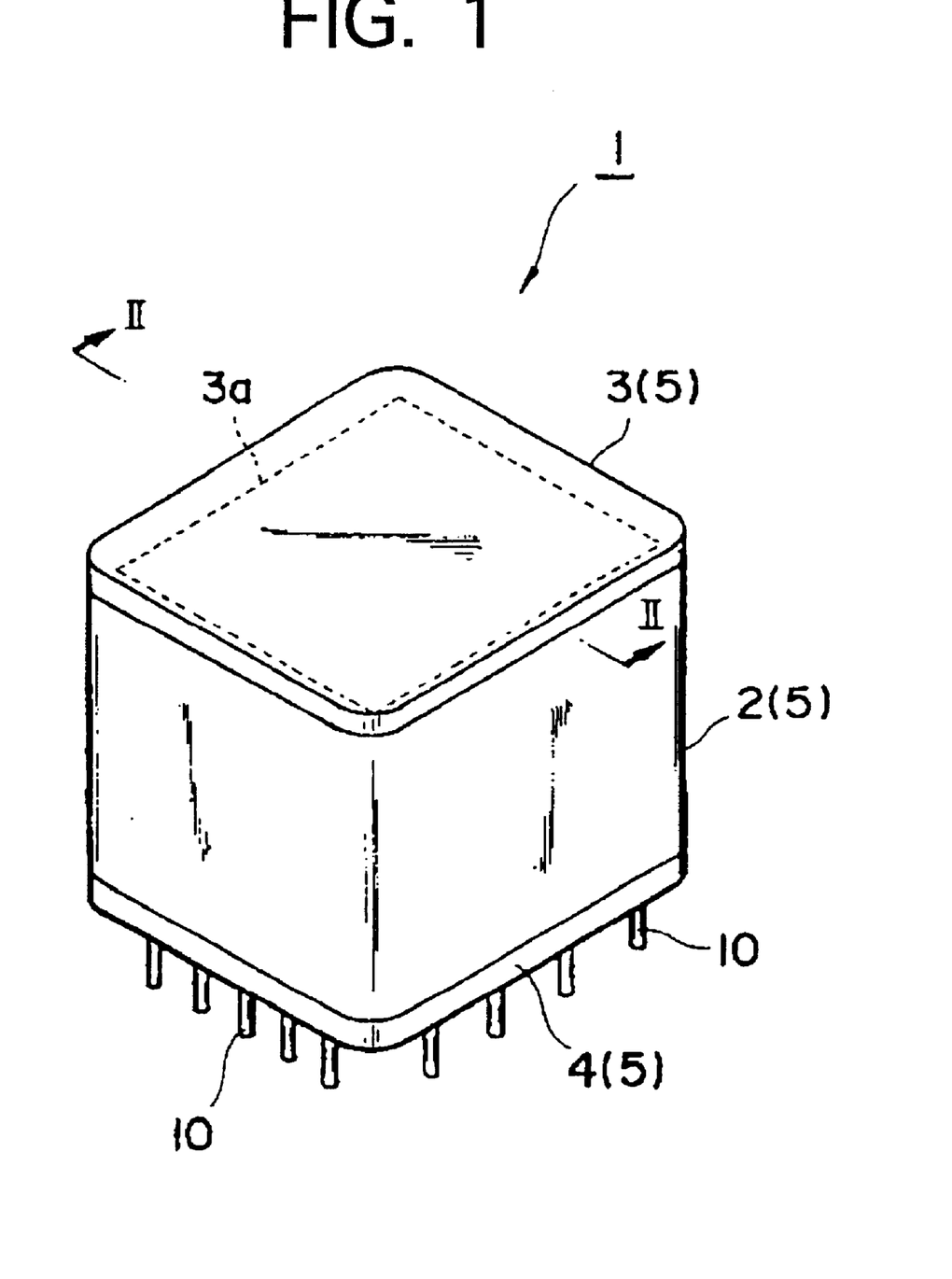
FIG. 1 is a perspective view showing a photomultiplier tube according to a first embodiment of the present invention.
Figure 2:
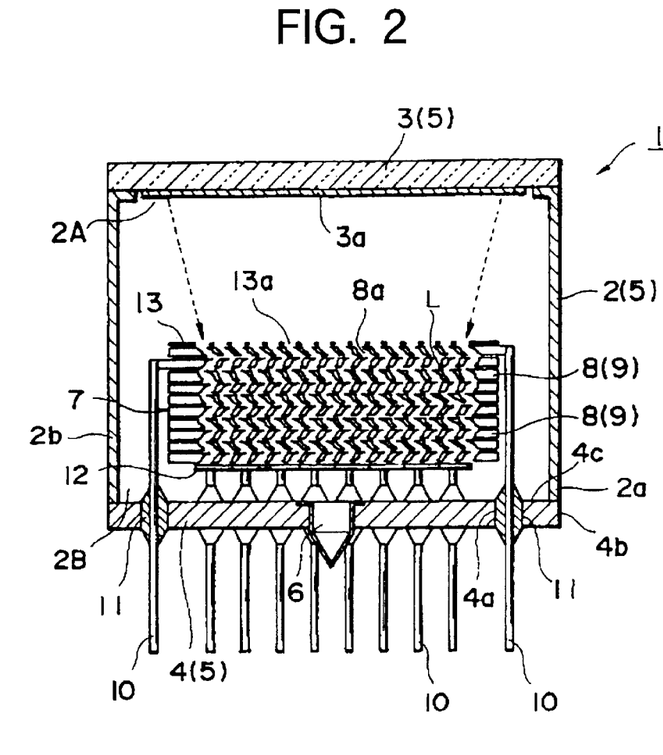
FIG. 2 is a cross-sectional view of the photomultiplier tube along the plane indicated by the arrows II in FIG. 1.

FIG. 1 is a perspective view showing a photomultiplier tube according to the first embodiment. FIG. 2 is a cross-sectional view of the photomultiplier tube in FIG. 1. A photomultiplier tube 1 shown in these figures includes a side tube 2 formed of a metallic material such as Kovar metal or stainless steel and shaped substantially like an angular cylinder and having an open end 2A on one end and an open end 2B on the other; a faceplate 3 formed of glass material that is fused to the open end 2A; and a stem plate 4 formed of a metal (such as Kovar metal or stainless steel) is fused to the open end 2B. A photocathode 3a is formed on the inner surface of the faceplate 3 for converting light into electrons. The photocathode 3a is formed by causing alkaline metal vapor to react to antimony that has been pre-deposited on the faceplate 3. Here, the side tube 2, faceplate 3, and stem plate 4 are the components that construct an airtight vessel 5.

A metal exhaust tube 6 is fixed in the center of the stem plate 4. After operations for assembling the photomultiplier tube 1 are completed, the exhaust tube 6 is used to evacuate the vessel 5 using a vacuum pump (not shown) and to introduce an alkaline metal vapor into the vessel 5 when forming the photocathode 3a.

A block-shaped layered electron multiplier 7 is disposed inside the vessel 5. The electron multiplier 7 includes a ten-stage electron multiplying section 9 that has ten plate-shaped dynodes 8 constructed in layers. The electron multiplier 7 is supported in the vessel 5 by a plurality of stem pins 10 formed of Kovar metal. The stem pins 10 penetrate the stem plate 4. Internal ends of each stem pin 10 connect electrically to each dynode 8. Pinholes 4a are formed in the stem plate 4 to allow each stem pin 10 to pass through. A tablet 11 made of Kovar glass fills each pinhole 4a to form a hermetic seal between each stem pin 10 and the stem plate 4. Each stem pin 10 is fixed to the stem plate 4 via the tablet 11. The stem pins 10 are arranged in a ring around the stem plate 4 near an edge surface 4b of the stem plate 4.

An insulation substrate (not shown) is disposed in the electron multiplier 7 at a position below the electron multiplying section 9. Anodes 12 are juxtaposed on top of this insulation substrate. A flat focusing electrode plate 13 is disposed on the top layer of the electron multiplier 7 between the photocathode 3a and the electron multiplying section 9 and is formed with a plurality of slits 13a that are arranged linearly in the same direction. Each dynode 8 in the electron multiplying section 9 is also formed with a plurality of slits 8a having the same number as the slits 13a and also arranged linearly in a single direction.

Each electron multiplying path L that is formed by the slits 8a and pass through all layers of the dynodes 8 is given a one-on-one correspondence to each slit 13a in the focusing electrode plate 13, thereby forming a plurality of linear channels in the electron multiplier 7. Each anode 12 that is provided in the electron multiplier 7 has a one-on-one correspondence to each channel. By connecting each anode 12 to each stem pin 10, it is possible to extract discrete output from the vessel 5 via each stem pin 10.

In this way, linear channels are formed in the electron multiplier 7. A prescribed voltage is supplied to the electron multiplying section 9 and the anode 12 by connecting the stem pins 10 to a bleeder circuit. The photocathode 3a and focusing electrode plate 13 are set to the same potential, while the dynodes 8 and anode 12 are set to increasingly higher potentials beginning from the top stage. Light striking the faceplate 3 is converted to electrons by the photocathode 3a. The electrons enter prescribed channels by the electron lens effect of the focusing electrode plate 13. While passing through the electron multiplying path L of the dynodes 8, the electrons multiply at each stage of the dynodes 8, impinging on the anode 12. As a result, the output from each channel can be obtained from each anode.

Next, a method of connecting the metal stem plate 4 to the side tube 2 formed of the same metal will be described.

Figure 3:
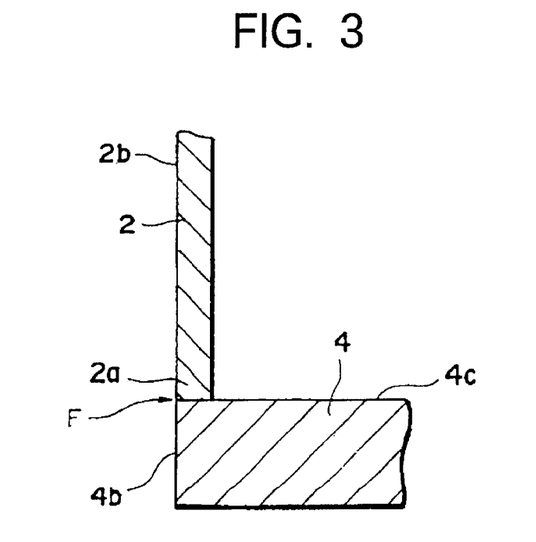
FIG. 3 is an enlarged cross-sectional view of the relevant part in FIG. 2.

According to the first embodiment of the present invention shown in FIG. 3, a bottom end 2a of the side tube 2 extending substantially in the axial direction of the tube is placed in contact with a top surface 4c of the stem plate 4, such that an outer surface 2b of the side tube 2 is flush with the edge surface 4b of the stem plate 4 along the axial direction. This construction eliminates protrusions such as a flange at the bottom of the photomultiplier tube 1. Referring to the point at which the bottom end 2a contacts the top surface 4c as a junction F, a laser beam external to the vessel 5 is irradiated directly horizontal and/or at a prescribed angle to the junction F, welding the two components together.

Next, other preferred embodiments of the present invention will be described regarding the junction between the stem plate 4 and the side tube 2. The basic construction and appearance of the photomultiplier tube in the various embodiments described below are substantially the same as that in the first embodiment. Therefore, like parts and components are designated by the same reference numerals to avoid duplicating description.

Figure 4:
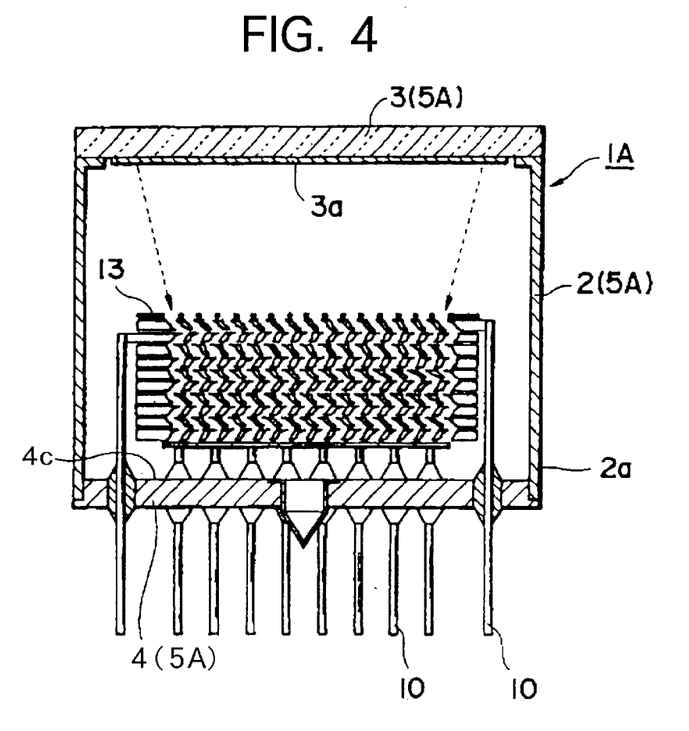
FIG. 4 is a cross-sectional view showing a photomultiplier tube according to a second embodiment.
Figure 5:
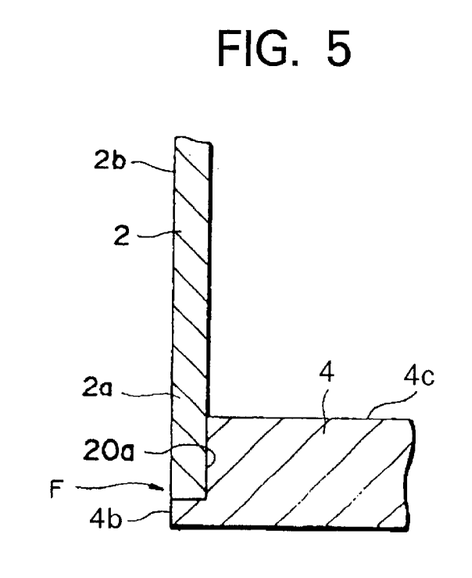
FIG. 5 is an enlarged cross-sectional view of the relevant part in FIG. 4.

FIGS. 4 and 5 show a photomultiplier tube according to a second embodiment of the present invention.

As shown in the drawings, a photomultiplier tube 1A has the metal stem plate 4. A cutout portion 20a is formed in the outer edge of the top surface 4c and has a step shape for placing the bottom end 2a of the side tube 2. The cutout portion 20a is formed in the top surface 4c around the entire edge of the stem plate 4 and has a rectangular ring shape that conforms to the shape of the side tube 2. The bottom end of the side tube 2 fits into the cutout portion 20a. The outer surface 2b is flush in the axial direction with the edge surface 4b.

By employing the fitting construction of the side tube 2 described above, the side tube 2 can be placed stably on the stem plate 4 before welding the junction F. Further, this construction facilitates positioning the side tube 2 over the stem plate 4. Moreover, after the junction F is welded, the reinforced construction can oppose a force toward the inside of the vessel 5A attempting to bend the side tube 2.

A laser beam external to the vessel 5A is irradiated directly horizontal to the junction F and/or at a prescribed angle to weld the components together. It is also possible to weld the junction F with an electron beam instead of the laser beam. In either case, the beams will not enter the vessel 5A during the welding process. Hence, the effects of heat on the internal parts can be avoided, as the formation of the side tube 2 prevents the beam from entering.

Figure 6:
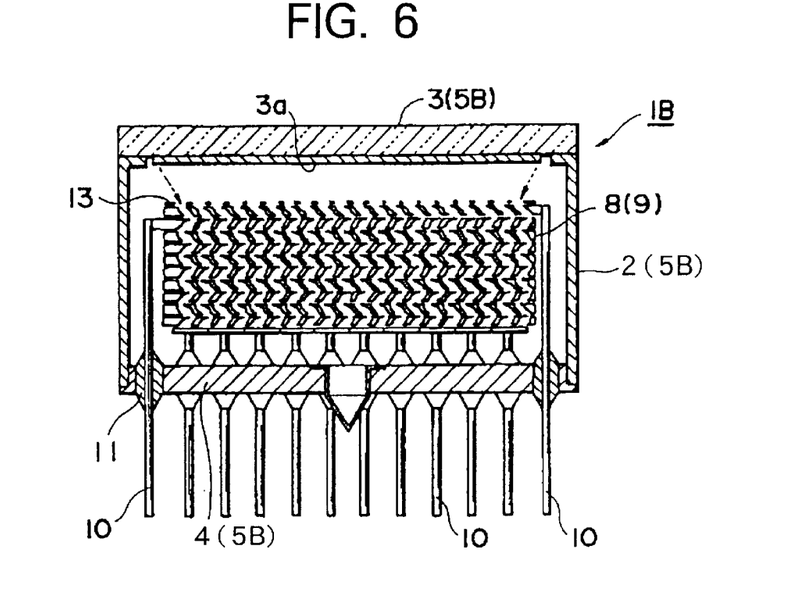
FIG. 6 is a cross-sectional view showing a photomultiplier tube according to a third embodiment.
Figure 7:
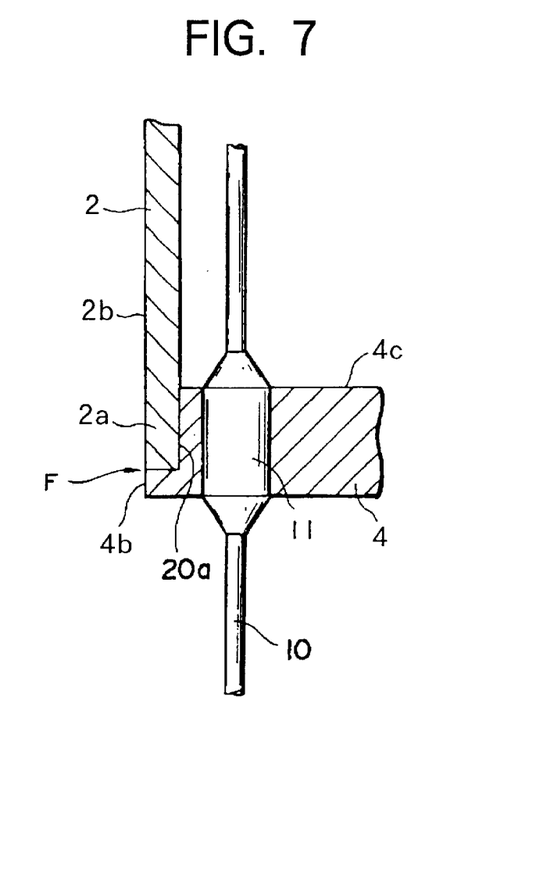
FIG. 7 is an enlarged cross-sectional view of the relevant part in FIG. 6.

FIGS. 6 and 7 show a photomultiplier tube 1B according to a third embodiment of the present invention.

In the photomultiplier tube 1B shown in FIG. 6, laser welding is employed to fuse the side tube 2 and stem plate 4 together, decreasing the amount of heat generated at the junction F. As a result, the stem pins 10 can be disposed near the side tube 2, as shown in FIG. 7, when the bottom end 2a is fit into the cutout portion 20a, such that the outer surface 2b and edge surface 4b are flush. This construction substantially prevents the effects of heat from generating cracks in the glass tablet 11 fixing the stem pins 10 to the stem plate 4. Accordingly, the stem pins 10 can be placed closer to the side tube 2, enabling the dynodes 8 to be expanded laterally. Such expansion increases the number of channels that can be formed in the electron multiplying section 9, providing a larger effective area in the electron multiplying section 9. By increasing the effective surface area in the electron multiplying section 9, it is possible to position the electron multiplying section 9 closer to the photocathode 3a, since the photoelectrons emitted from the photocathode 3a toward the focusing electrode plate 13 do not move at a large angle. This construction enables the height dimension of the vessel 5B to be reduced, thereby forming a compact photomultiplier tube having a larger effective surface area.

With conventional resistance welding, a distance of approximately 3.5 mm must be formed between the edge of the stem plate 4 and the center of the stem pins 10. Using laser beam or electron beam welding, however, it has been confirmed that a distance of 1.1 mm is sufficient. While the distance from the photocathode 3a to the focusing electrode plate 13 in the photomultiplier tube 1A of FIG. 4 is 7 mm, the lateral expansion of the electron multiplying section 9 in the photomultiplier tube 1B of FIG. 6 enables this distance to be reduced to 2.5 mm. By employing the laser beam or electron beam welding method, it is not only possible to eliminate the flange from the photomultiplier tube, but also to reduce the height dimension, thereby making great advances toward producing a compact photomultiplier tube.

When densely juxtaposing a plurality of photomultiplier tubes, the existence of a flange on the outside of the photomultiplier tubes has a great effect on this arrangement, particularly as the external dimensions decrease. For example, if an angular side tube 2 has external side dimensions of 25 mm and if the flange used for resistance welding has a width of 2 mm and protrudes externally around the entire edge of the tube, the flange portion occupies nearly 20 percent of the dimensions of the tube. Arranging this type of photomultiplier tube in a dense formation would generate a large proportion of dead space.

Figure 8:
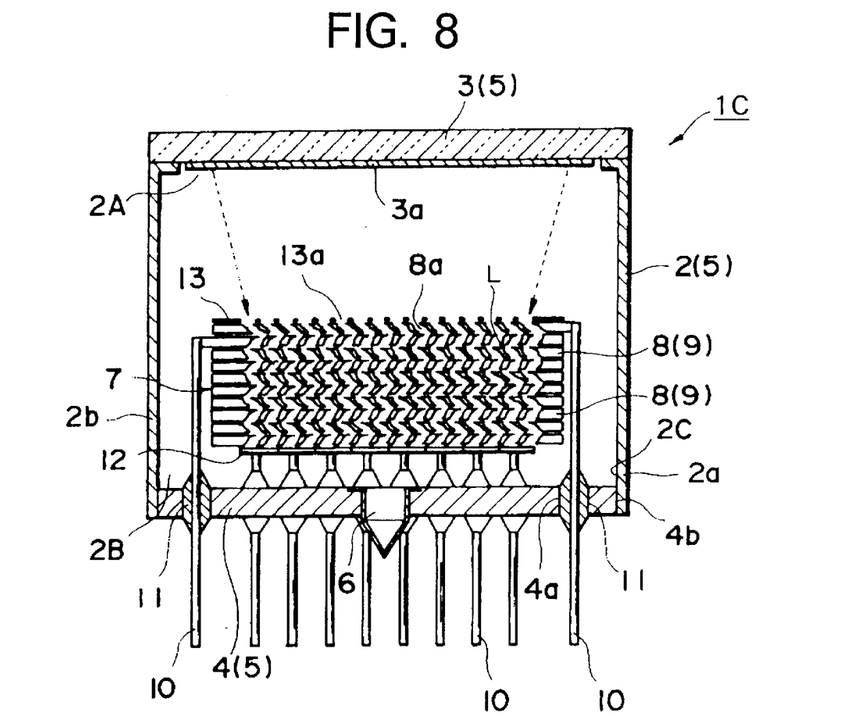
FIG. 8 is a cross-sectional view showing a photomultiplier tube according to a fourth embodiment.
Figure 9:
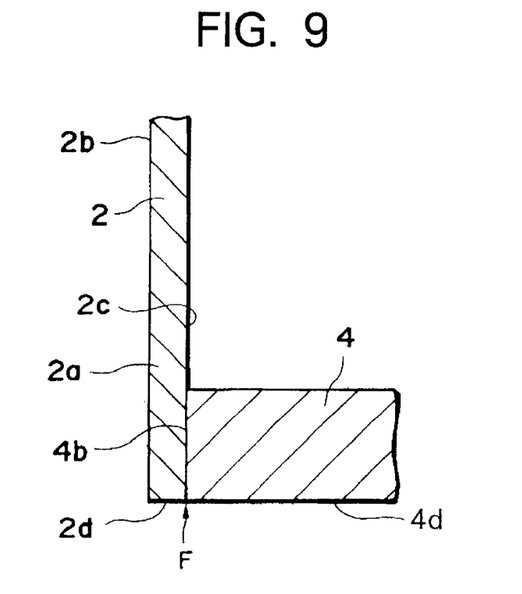
FIG. 9 is an enlarged cross-sectional view of the relevant part in FIG. 8.

FIGS. 8 and 9 show a photomultiplier tube according to a fourth embodiment of the present invention.

When forming an airtight weld between the stem plate 4 and side tube 2 shown in FIG. 9, the stem plate 4 is inserted into the open end 2B of the side tube 2, such that an inner surface 2c on the bottom end 2a contacts the edge surface 4b. At this time, a bottom surface 4d of the stem plate 4 is flush with a bottom end surface 2d of the side tube 2 in order that the bottom end surface 2d does not protrude lower than the stem plate 4. Accordingly, the outer surface 2b along the bottom end 2a extends substantially in the axial direction, and the flange protrusion is eliminated from the bottom end of the photomultiplier tube 1C. When welding the junction F, a laser beam external to the photomultiplier tube 1C is radiated from directly beneath the junction F. Eliminating a flange-like protrusion from the bottom of the photomultiplier tube 1C poses difficulties for resistance welding. However, this construction allows the external dimensions of the photomultiplier tube 1C to be reduced and helps to eliminate as much dead space as possible when juxtaposing a plurality of photomultiplier tube 1C, by enabling the side tubes 2 to be positioned close to one another. Accordingly, employing a laser welding method to join the stem plate 4 and side tube 2 can help reduce the size of the photomultiplier tube 1C and enables such photomultiplier tube 1C to be more densely packed together.

Figure 10:
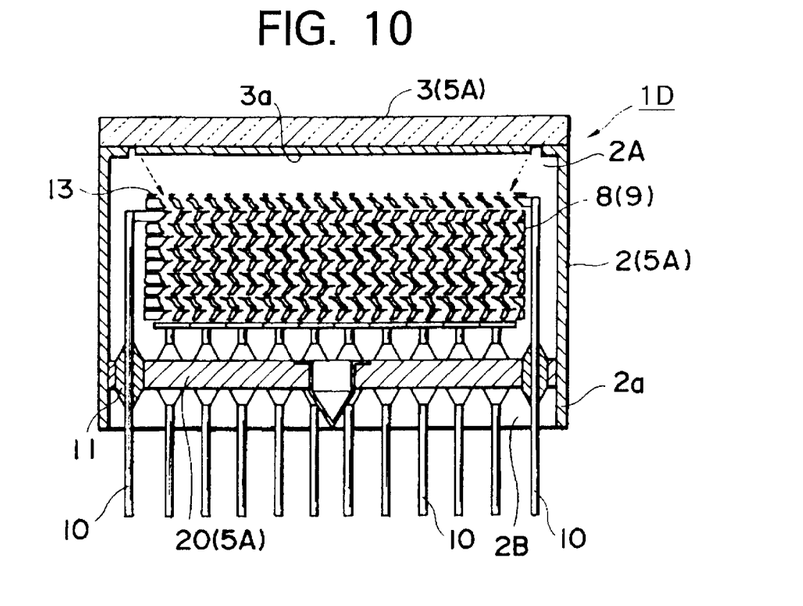
FIG. 10 is a cross-sectional view showing a photomultiplier tube according to a fifth embodiment.
Figure 11:
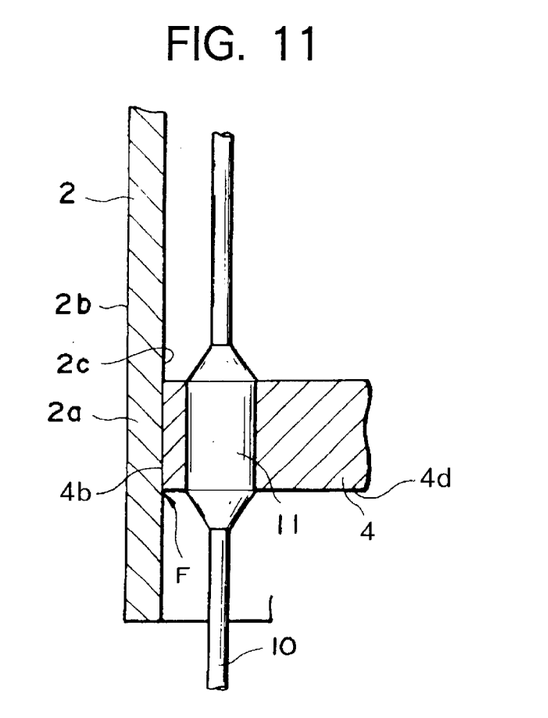
FIG. 11 is an enlarged cross-sectional view of the relevant part in FIG. 10.

FIGS. 10 and 11 show a photomultiplier tube according to a fifth embodiment of the present invention.

As shown in FIGS. 10 and 11, a photomultiplier tube 1D is formed such that the bottom end 2a has a free end extending in the axial direction. Hence, the stem plate 4 is inserted through the open end 2B, such that the edge surface 4b contacts and slides inwardly on the inner surface 2c of the bottom end 2a. With this configuration, the distance between the top layer of the dynodes 8 in the electron multiplying section 9, which is fixed to the stem plate 4, and the photocathode 3a can easily be adjusted before the welding process to suit the need. This is performed simply by pushing on the bottom surface 4d of the stem plate 4 toward the inside of the side tube 2. Although the side tube 2 in the photomultiplier tube 1D shown in FIG. 10 extends in the axial direction of the tube, the side tube 2 can also be formed such that the open end 2B is wider than the open end 2A to facilitate insertion of the stem plate 4 into the photomultiplier tube 1D.

When employing laser welding to weld the junction F, it is possible to decrease the heat generated at the junction F. Hence, as described in the third embodiment shown in FIGS. 6 and 7, the stem pins 10 can be positioned closer to the side tube 2, thereby producing a more compact photomultiplier tube of the same size described in the third embodiment.

Figure 12:
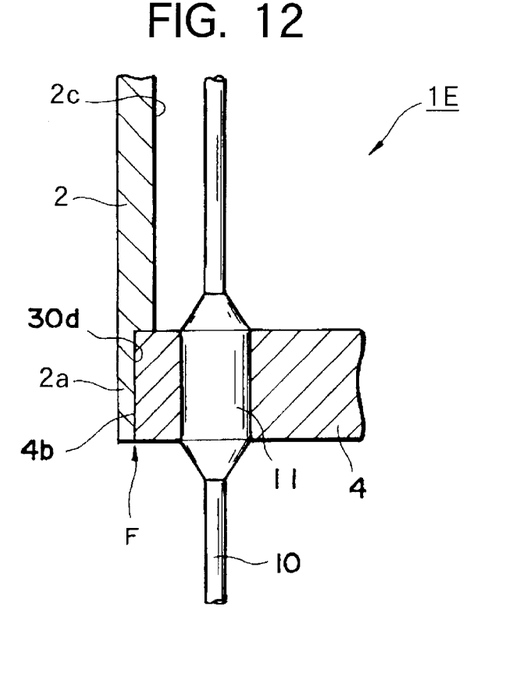
FIG. 12 is a cross-sectional view showing the relevant part of a photomultiplier tube according to a sixth embodiment.

FIG. 12 shows a photomultiplier tube according to the sixth embodiment of the present invention.

In a photomultiplier tube 1E of the sixth embodiment, a cutout portion 30d having a cross section shaped as the letter L is formed in the inner surface 2c. The cutout portion 30d enables the outer edge of the stem plate 4 to be inserted therein. The cutout portion 30d forms a rectangular ring around the entire inner surface 2c and conforms to the outer shape of the stem plate 4. By employing this construction, it is possible to rest the side tube 2 stably on the stem plate 4 before welding the junction F, thereby easily positioning the side tube 2 in relation to the stem plate 4. Moreover, the interval between the top layer of the dynodes 8 in the electron multiplying section 9, which is fixed to the stem plate 4, and the photocathode 3a formed on the faceplate 3 can be easily set by adjusting the depth of the cutout portion 30d.

The junction F is welded by irradiating a laser beam thereon. It is also possible to use an electron beam in place of the laser beam. In either case, the beam does not enter the evacuated vessel during the welding process, thereby avoiding heat affecting the internal components, since the cutout portion 30d blocks the penetration of such beams.

Figure 13:
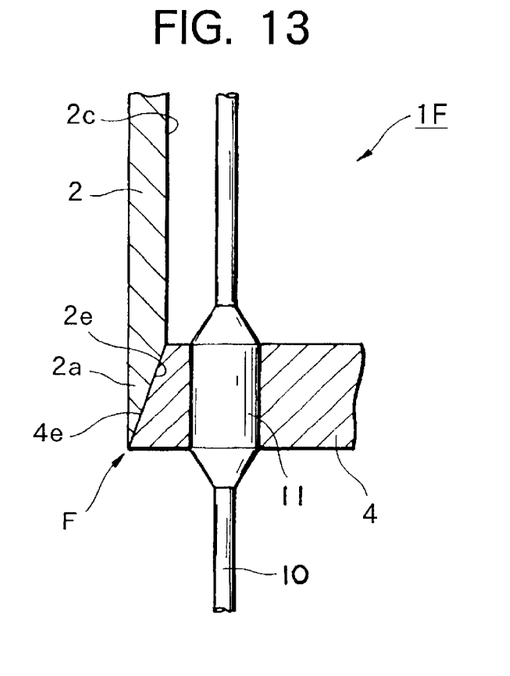
FIG. 13 is a cross-sectional view showing the relevant part of a photomultiplier tube according to a seventh embodiment.

FIG. 13 shows a photomultiplier tube according to the seventh embodiment of the present invention.

In a photomultiplier tube 1F of the seventh embodiment, a tapered surface 2e is formed in the inner surface 2c of the bottom end 2a and a tapered edged surface 4e is formed in the stem plate 4. The tapered surface 2e forms a rectangular ring around the entire inner surface 2c and conforms to the tapered edged surface 4e of the stem plate 4. By employing this construction, it is possible to rest the side tube 2 stably on the stem plate 4 before welding the junction F, thereby easily positioning the side tube 2 in relation to the stem plate 4.

Figure 14:
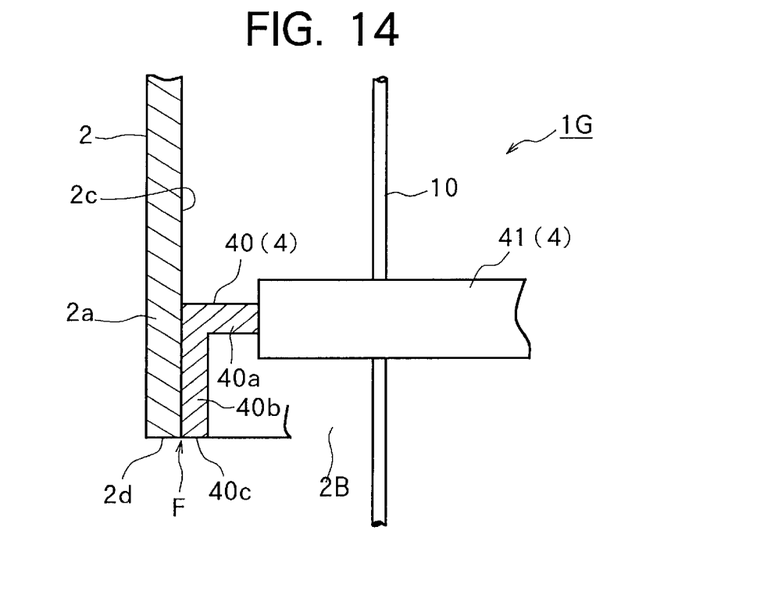
FIG. 14 is a cross-sectional view showing the relevant part of a photomultiplier tube according to an eighth embodiment.

FIG. 14 shows a photomultiplier tube according to the eighth emodiment of the present invention.

A photomultiplier tube 1G of the eighth embodiment includes a metal stem support member 40 that contacts the inner surface 2c of the bottom end 2a; and a glass stem plate 41 that is square-shaped and planar and supported by this stem support member 40. The stem support member 40 has a cross-section substantially shaped like the letter L having a horizontal portion 40a and a vertical portion 40b. The horizontal portion 40a is fixed to each side surface of the stem plate 41. The vertical portion 40b extends in the axial direction of the tube while contacting the inner surface 2c. A bottom end surface 40c of the vertical portion 40b is flush with the outer surface 2b. The stem pins 10 penetrate the stem plate 41. In the first to seventh embodiments, the tablets 11 formed of Kovar glass fill each pinhole 4a through which the stem pins 10 penetrate, in order to maintain insulation between the stem pins 10 and the metal stem plate 4. In the present embodiment, however, the tablets 11 are unnecessary because the stem pins 10 penetrate a glass stem plate 41, which is formed of glass.

In order to manufacture the photomultiplier tube 1G of the present embodiment, the stem support member 40 is prefixed to all sides of the stem plate 41, thereby forming the stem plate 4. The stem plate 4 is inserted into the side tube 2 through the open end 2B, sliding the edge surface 4b in contact with the inner surface 2c. The stem plate 4 is slid into the side tube 2 until the bottom end surface 40c is flush with the bottom end surface 2d. The junction F is welded by a laser.

In the present embodiment, the interval between the top layer of the dynodes 8 in the electron multiplying section 9, which is fixed to the stem plate 4, and the photocathode 3a formed on the faceplate 3 can be regulated by adjusting the length of the vertical portion 40b.

Figure 15:
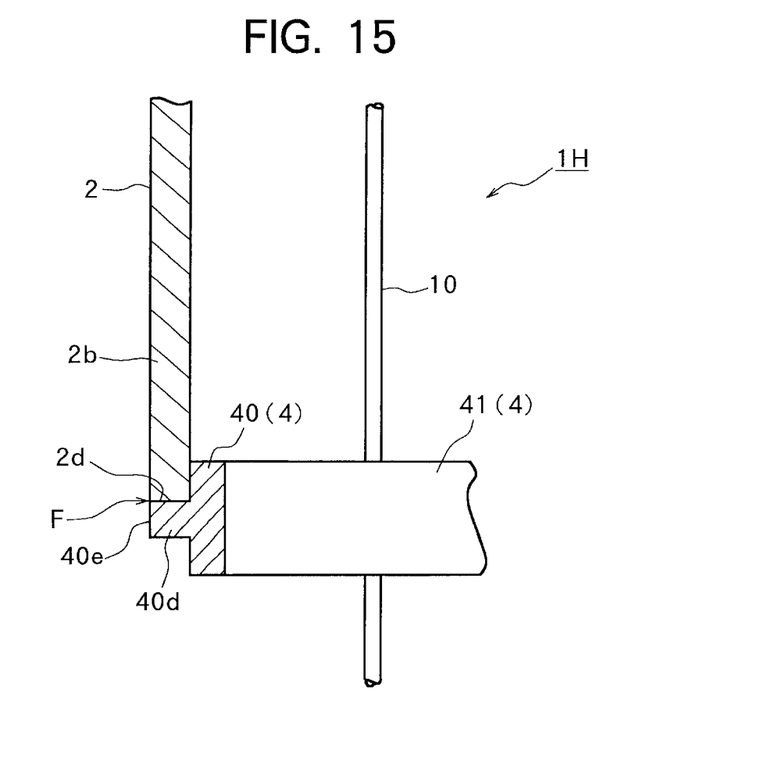
FIG. 15 is a cross-sectional view showing the relevant part of a photomultiplier tube according to a ninth embodiment.

FIG. 15 shows a photomultiplier tube according to a eighth embodiment of the present invention. Similar to the ninth embodiment shown in FIG. 14, a photomultiplier tube 1H shown in FIG. 15 includes the stem plate 4 configured of the stem support member 40 and the stem plate 41, wherein the stem plate 4 is welded to the bottom end 2a to form an airtight seal. The stem support member 40 has a cross section shaped substantially like the letter T. The top surface of a horizontal protrusion 40d of the stem support member 40 contacts the bottom end surface 2d of the side tube 2, such that an edge surface 40e of the horizontal protrusion 40d is flush with the outer surface 2b in the axial direction of the side tube 2.

The horizontal protrusion 40d of the stem support member 40 is preprocessed to have a protruding length equivalent to the thickness of the side tube 2. With this configuration, it is possible to mount the side tube 2 stably on the stem plate 4 prior to laser welding the junction F, facilitating the positioning of the side tube 2.

The photomultiplier tubes in all the embodiments described above are constructed without a flange-like protrusion. As a result, it is difficult to join the stem plate 4 and side tube 2 using the resistance welding method that is employed in the conventional method. However, the junction can be joined through laser welding. As a result, the present invention can reduce the dimensions of the photomultiplier tube, thereby eliminating as much dead space as possible when a plurality of photomultiplier tubes are arranged together, enabling the side tubs 2 to be disposed near one another. Hence, the use of laser welding to join the stem plate 4 and side tube 2 can reduce the size of the photomultiplier tube and enable more densely packed arrays.

Further, the use of a laser for welding the side tube 2 to the stem plate 4 differs from resistance welding by eliminating the need to apply pressure on the side tube 2 and the stem plate 4 at the junction F. Accordingly, residual stress is not generated at the junction F. This makes it unlikely for cracking to occur during use at the junctions and greatly helps improve the durability of the apparatus and strengthens the hermetic seal.

In the embodiments described above, laser welding was used as the example for welding the side tube 2 and the stem plate 4 together. However, it is also possible to use an electron beam in place of the laser beam. Since both laser beam and electron beam welding can reduce the amount of heat generated at the junction F compared to that generated during resistance welding, the effects of heat on components mounted in the vessel 5 is extremely small when assembling the photomultiplier tube.

Next, the example of a radiation detector employing a plurality of photomultiplier tubes densely packed together will be described. For convenience sake, the photomultiplier tube 1 shown in FIG. 1 will be used in the description, although the same radiation detector can be constructed using a photomultiplier tube described in any of the embodiments above.

Figure 16:
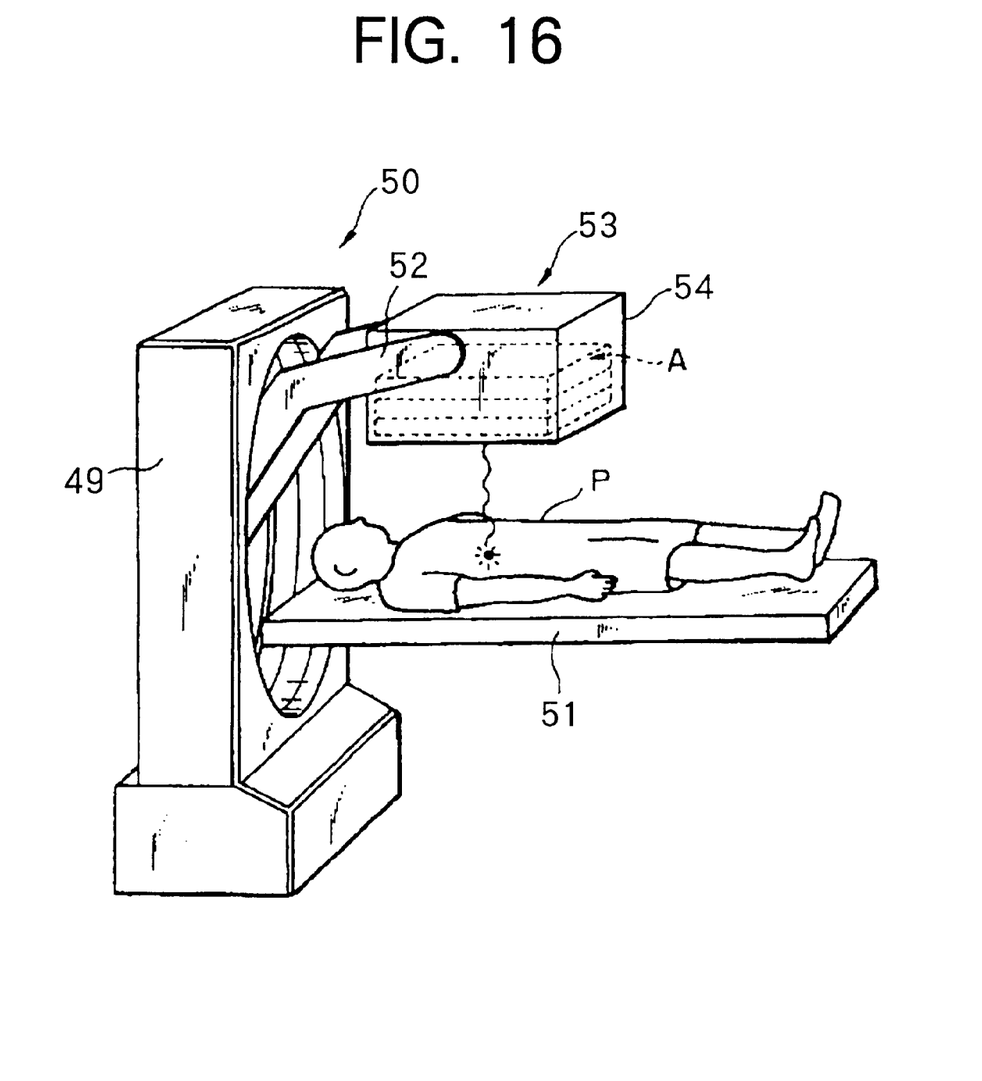
FIG. 16 is a perspective view showing a type of radiation detector employing the photomultiplier tube according to the present invention.

As shown in FIG. 16, a gamma camera 50 serves as the radiation detector of the present example. The gamma camera 50 was developed in nuclear medicine as a diagnostic apparatus. The gamma camera 50 includes a support frame 49; arms 52 extending from the support frame 49; a detector 53 supported by the arms 52; and a bed 51 positioned directly underneath the detector 53 for supporting a prostrated patient to be examined.

Figure 17:
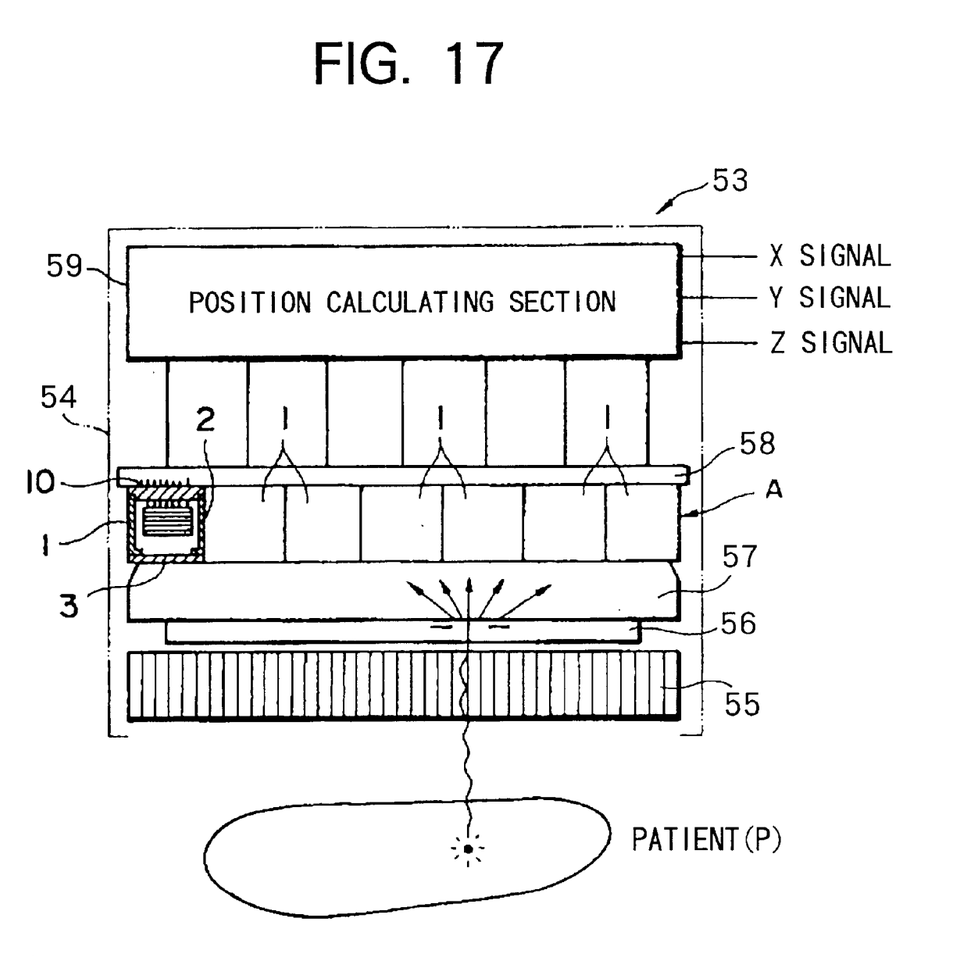
FIG. 17 is a side view showing the internal structure of the radiation detector of FIG. 16.

As shown in FIG. 17, the detector 53 includes an outer casing 54; a collimator 55 provided at the bottom level of the outer casing 54 at a position opposing the diseased part of the patient; a scintillator 56 disposed above the collimator 55 in the outer casing 54; a group of photomultiplier tubes A; and a light guide 57 for fixing the scintillator 56 to the group of photomultiplier tubes A. The group of photomultiplier tubes A includes a plurality of the photomultiplier tubes 1 juxtaposed. The faceplates 3 of the photomultiplier tubes 1 face downward in opposition to the scintillator 56 since the scintillator 56 emit fluorescent light onto the faceplate 3 via the light guide 57.

Figure 18:
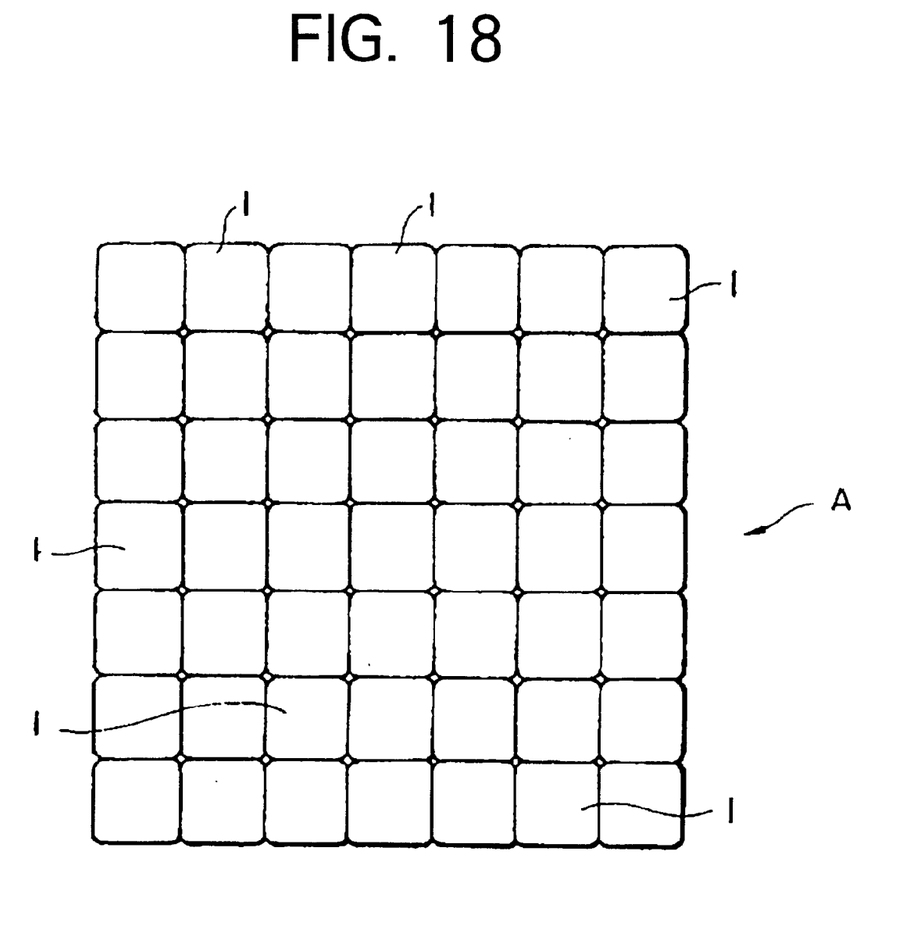
FIG. 18 is a plan view showing the photomultiplier tubes of FIG. 1 arranged in a matrix formation.

When using the plate-shaped scintillator 56, the group of photomultiplier tubes A is arranged in a densely packed matrix formation, as shown in FIG. 18, wherein the side tubes 2 of the photomultiplier tubes 1 are in close contact with one another. The matrix formation of the group of photomultiplier tubes A is achieved by inserting and fixing the stem pins 10 of each photomultiplier tube 1 into a socket member 58. In addition, a position calculating section 59 for computing processes based on charges output from each stem pin 10 of each photomultiplier tube 1 is provided in the outer casing 54. The position calculating section 59 outputs an X signal, Y signal, and Z signal for creating a 3-dimensional image on a display monitor (not shown). The light guide 57 converts gamma rays generated from the diseased part of the patient into prescribed fluorescent light. Each of the photomultiplier tube 1 converts this fluorescent energy into electrical charges, after which the position calculating section 59 outputs the charges externally as position signals. In this way, the distribution of radiation energy can be displayed on the monitor for use in diagnoses.

In the brief example above, the gamma camera 50 is used as the radiation detector. However, another example of a radiation detector used in nuclear medicine diagnoses is a positron CT, known as a PET. It is obvious that a plurality of photomultiplier tube 1 according to the present invention can also be employed in this apparatus.

INDUSTRIAL APPLICABILITY

The photomultiplier tube of the present invention can be used as an optical analyzing apparatus that utilizes absorption, reflection, and polarization of specific wavelengths to analyze diverse matter. Such an apparatus has applications in a wide variety of apparatus, including medical equipment, analysis equipment, and industrial instruments.

What is claimed is:

1. A photomultiplier tube having a faceplate (3), a photocathode (3a) for emitting electrons in response to light incident on the faceplate (3), an electron multiplying section (9), disposed inside an airtight vessel (5), for multiplying the electrons emitted from the photocathode (3a), and an anode (12) for outputting an output signal based on the electrons multiplied by the electron multiplying section (9), characterized in that the airtight vessel (5) is formed by:

a stem plate (4) for fixedly supporting the electron multiplying section (9) and the anode (12) with stem pins (10);

a side tube (2) with the stem plate (4) fixed on one open end, the side tube (2) being formed of metal and enclosing the electron multiplying section (9) and the anode (12); and the faceplate (3) fixed on the other open end of the side tube (2), and that an inner surface of a lower portion of the side tube (2) is in contact with an outer edge of the stem plate (4) so that the lower portion of the side tube does not extend beyond other portions of the side tube, at least a portion of the stem plate (4) contacting the inner surface of the lower portion of the side tube (2) is formed of metal, the portion thereof including the outer edge of the stem plate (4), and the side tube (2) is welded to the stem plate (4).

2. The photomultiplier tube as recited in claim 1, wherein the side tube has a free end at the lower portion thereof, allowing the stem plate to slide along the inner surface of the side tube.

3. The photomultiplier tube as recited in claim 1, wherein the metal side tube is fusion welded to the stem plate.

4. The photomultiplier tube as recited in claim 3, wherein the fusion welding is laser welding or electron beam welding.

5. The photomultiplier tube as recited in claim 1, wherein entirety of the stem plate is formed of metal.

6. The photomultiplier tube as recited in claim 1, wherein the stem plate comprises a metal stem support member, and a glass stem plate, the metal stem support member being in contact with the inner surface of the lower portion of the side tube.

7. The photomultiplier tube as recited in claim 1, wherein a tapered surface is formed in the inner surface of the lower portion of the side tube and a tapered edged surface is formed in the stem plate to conform to the tapered surface of the side tube, and the tapered surface of the side tube and the tapered edged surface of the stem plate are in contact with each other.

8. The photomultiplier tube as recited in claim 1, wherein a bottom surface of the stem plate and a bottom surface of the side tube are flush with each other.

* * * * *